US00PP30233P2

(12) United States Plant Patent
Wood

(10) Patent No.: US PP30,233 P2
(45) Date of Patent: Feb. 26, 2019

(54) ***ITEA* PLANT NAMED 'SMNIVDFC'**

(50) Latin Name: *Itea virginiana*
Varietal Denomination: SMNIVDFC

(71) Applicant: Timothy D. Wood, Spring Lake, MI (US)

(72) Inventor: Timothy D. Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 15/732,302

(22) Filed: Oct. 20, 2017

(51) Int. Cl.
*A01H 5/00* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Itea* plant named 'SMNIVDFC', characterized by its upright to outwardly spreading plant habit; freely branching habit, dense and bushy appearance; attractive autumnal leaf color; freely flowering habit; fragrant white-colored flowers; and good garden performance.

2 Drawing Sheets

Botanical designation: *Itea virginiana.*
Cultivar denomination: 'SMNIVDFC'.

BACKGROUND OF THE INVENTION

The present invention relates to a new and distinct *Itea* plant, botanically known as *Itea virginiana*, commonly referred to as Virginia Sweetspire and hereinafter referred to by the name 'SMNIVDFC'.

The new *Itea* plant is a product of a planned breeding program conducted by the Inventor in Grand Haven, Mich. The objective of the breeding program was to create new freely-branching *Itea* plants with fragrant flowers and attractive autumn leaf coloration.

The new *Itea* plant originated from an open-pollination in 2011 in Grand Haven, Mich. of an unnamed seedling selection of *Itea virginiana*, not patented, as the female, or seed, parent with an unknown selection of *Itea virginiana* as the male, or pollen, parent. The new *Itea* plant was discovered and selected by the Inventor as a single plant within the progeny of the stated open-pollination in a controlled environment in Grand Haven, Mich. in 2014.

Asexual reproduction of the new *Itea* plant by softwood stem cuttings in a controlled environment in Grand Haven, Mich. since 2014 has shown that the unique features of this new *Itea* plant are stable and reproduced true to type in successive generations.

SUMMARY OF THE INVENTION

Plants of the new *Itea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNIVDFC'. These characteristics in combination distinguish 'SMNIVDFC' as a new and distinct *Itea* plant:

1. Upright to outwardly spreading plant habit.
2. Freely branching habit, dense and bushy appearance.
3. Attractive autumnal leaf color.
4. Freely flowering habit.
5. Fragrant white-colored flowers.
6. Good garden performance.

Plants of the new *Itea* differ primarily from plants of the female parent selection in the following characteristics:

1. During the summer, leaves of plants of the new *Itea* are darker green in color than leaves of plants of the female parent selection.
2. During the autumn, leaves of plants of the new *Itea* are darker red and purple in color than leaves of plants of the female parent selection.
3. Flowers of plants of the new *Itea* are more fragrant than flowers of plants of the female parent selection.

Plants of the new *Itea* can also be compared to plants of *Itea virginiana* 'Sprich', disclosed in U.S. Plant Pat. No. 10,988. In side-by-side comparisons, plants of the new *Itea* differ primarily from plants of 'Sprich' in the following characteristics:

1. During the summer, leaves of plants of the new *Itea* are darker green in color than leaves of plants of 'Sprich'.
2. During the autumn, leaves of plants of the new *Itea* are darker red and purple in color than leaves of plants of 'Sprich'.

BRIEF DESCRIPTION OF THE PHOTOGRAPHS

The accompanying colored photographs illustrate the overall appearance of the new *Itea* plant showing the colors as true as it is reasonably possible to obtain in colored reproductions of this type. Colors in the photographs may differ slightly from the color values cited in the detailed botanical description which accurately describe the colors of the new *Itea* plant.

The photograph on the first sheet is a side perspective view of a typical flowering plant of 'SMNIVDFC' grown during the summer.

The photograph on the second sheet is a close-up view of a typical plant of 'SMNIVDFC' during the autumn.

DETAILED BOTANICAL DESCRIPTION

The aforementioned photographs and following observations, measurements and values describe plants grown during the spring, summer and autumn in three-gallon containers in a polyethylene-covered greenhouse in Grand Haven, Mich. and under cultural practices typical of commercial production. Plants were two years old when the photographs and description were taken. During the production of the plants, day temperatures ranged from 18° C. to 27° C. and night temperatures ranged from 5° C. to 10° C. In the following description, color references are made to The Royal Horticultural Society Colour Chart, 2015 Edition, except where general terms of ordinary dictionary significance are used.

Botanical classification: *Itea virginiana* 'SMNIVDFC'.

Parentage:

*Female, or seed, parent*.—Unnamed seedling selection of *Itea virginiana*, not patented.

*Male, or pollen, parent*.—Unknown selection of *Itea virginiana*, not patented.

Propagation:

*Type*.—By softwood stem cuttings.

*Time to initiate roots plant, summer*.—About three to four weeks at temperatures ranging from 18° C. to 27° C.

*Time to produce a rooted plant, summer*.—About three months at temperatures ranging from 18° C. to 27° C.

*Root description*.—Fine, fibrous; typically white in color, actual color of the roots is dependent on substrate composition, water quality, fertilizer, substrate temperature and physiological age of roots.

*Rooting habit*.—Moderately freely branching; dense.

Plant description:

*Plant and growth habit*.—Deciduous perennial shrub; upright and outwardly spreading plant habit; dense and bushy appearance; vigorous growth habit.

*Plant height*.—About 80 cm.

*Plant width* (*spread*).—About 80 cm.

*Lateral branches*.—Quantity: Freely branching habit with about ten primary lateral branches developing per plant; pinching enhances lateral branch development. Length: About 53 cm. Diameter: About 5 mm. Internode length: About 2 cm. Strength: Strong. Aspect: Erect to about 90° from vertical. Texture: Smooth, glabrous. Color: Close to 138A.

Leaf description:

*Arrangement*.—Alternate, simple.

*Length*.—About 6 cm.

*Width*.—About 2.5 cm.

*Shape*.—Elliptical.

*Apex*.—Acute.

*Base*.—Attenuate.

*Margin*.—Serrate.

*Texture, upper surface*.—Smooth, glabrous.

*Texture, lower surface*.—Slightly rough with prominent venation, glabrous.

*Venation pattern*.—Pinnate.

*Color, developing leaves, upper surface*.—Spring: Close to 179A mixed with close to 145A. Summer: Close to 137A. Autumn: Close to N79B.

*Color, developing leaves, lower surface*.—Spring: Close to 179A mixed with close to 145A. Summer: Close to 137D. Autumn: Close to 36D.

*Color, fully expanded leaves, upper surface*.—Spring: Close to 143A. Summer: Close to 137A; venation, close to N144B. Autumn: Multiple colors, close to N79B, 41C and 53C.

*Color, fully expanded leaves, lower surface*.—Spring: Close to 143C. Summer: Close to 137D; venation, close to 142C. Autumn: Close to 36D.

*Petioles*.—Length: About 5 mm. Diameter: About 1 mm. Texture, upper and lower surfaces: Smooth, glabrous. Color, upper surface: Close to 180B. Color, lower surface: Close to 180D.

Flower description:

*Flower type and flowering habit*.—Single small star-shaped flowers arranged on terminal and axillary racemes; inflorescences face upright, outwardly or are drooping; racemes narrowly conical in shape; freely flowering habit with more than 100 flowers developing per inflorescence; flowers face upright to outwardly depending on position on the raceme; flowers persistent.

*Fragrance*.—Fragrant, earthy; pleasant.

*Natural flowering season*.—Plants flower continuously from during the spring in Michigan.

*Flower buds*.—Height: About 4 mm. Diameter: About 2 mm. Shape: Ovoid. Color: Close to 157B.

*Inflorescence length*.—About 7 cm.

*Inflorescence diameter*.—About 2 cm.

*Flower diameter*.—About 1 cm.

*Flower depth*.—About 4 mm.

*Petals*.—Quantity per flower: Typically five in a single whorl. Length: About 5 mm. Width: About 1 mm. Shape: Acicular. Apex: Acute. Base: Truncate. Margin: Entire. Texture, upper and lower surfaces: Smooth, glabrous. Color: Developing petals, upper and lower surfaces: Close to NN155D. Fully developed petals, upper and lower surfaces: Close to NN155D.

*Calyx*.—Length: About 2 mm. Diameter: About 2 mm. Shape: Cup-shaped. Quantity of sepals per flower: Typically five in a single whorl. Sepal length: About 2 mm. Sepal width: Less than 1 mm.

*Peduncles*.—Length: About 2.5 cm. Diameter: About 2 mm. Strength: Strong, flexible. Angle: Upright to outwardly. Texture: Slightly pubescent. Color: Close to 144A.

*Pedicels*.—Length: About 2 mm. Diameter: About 1 mm. Strength: Strong, flexible. Texture: Smooth, glabrous. Color: Close to 144A.

*Reproductive organs*.—Stamens: Quantity per flower: Typically five. Filament length: About 2 mm. Filament color: Close to NN155D. Anther length: Less than 1 mm. Anther shape: Globular. Anther color: Close to NN155D. Pollen amount: Moderate. Pollen color: Close to NN155D. Pistils: Quantity per flower: One. Pistil length: About 1.5 mm. Style length: Less than 1 mm. Style color: Close to NN155D. Stigma shape: Rounded. Stigma color: Close to NN155D.

*Seeds and fruits*.—Seed and fruit development have not been observed on plants of the new *Itea* to date.

Disease & pest resistance: Plants of the new *Itea* have not been observed to be resistant to pathogens and pests common to *Itea* plants to date.

Garden performance: Plants of the new *Itea* have been observed to have good garden performance and tolerate rain, wind and to tolerate temperatures ranging from about −32° C. to about 36° C.

It is claimed:

1. A new and distinct *Itea* plant named 'SMNIVDFC' as illustrated and described.

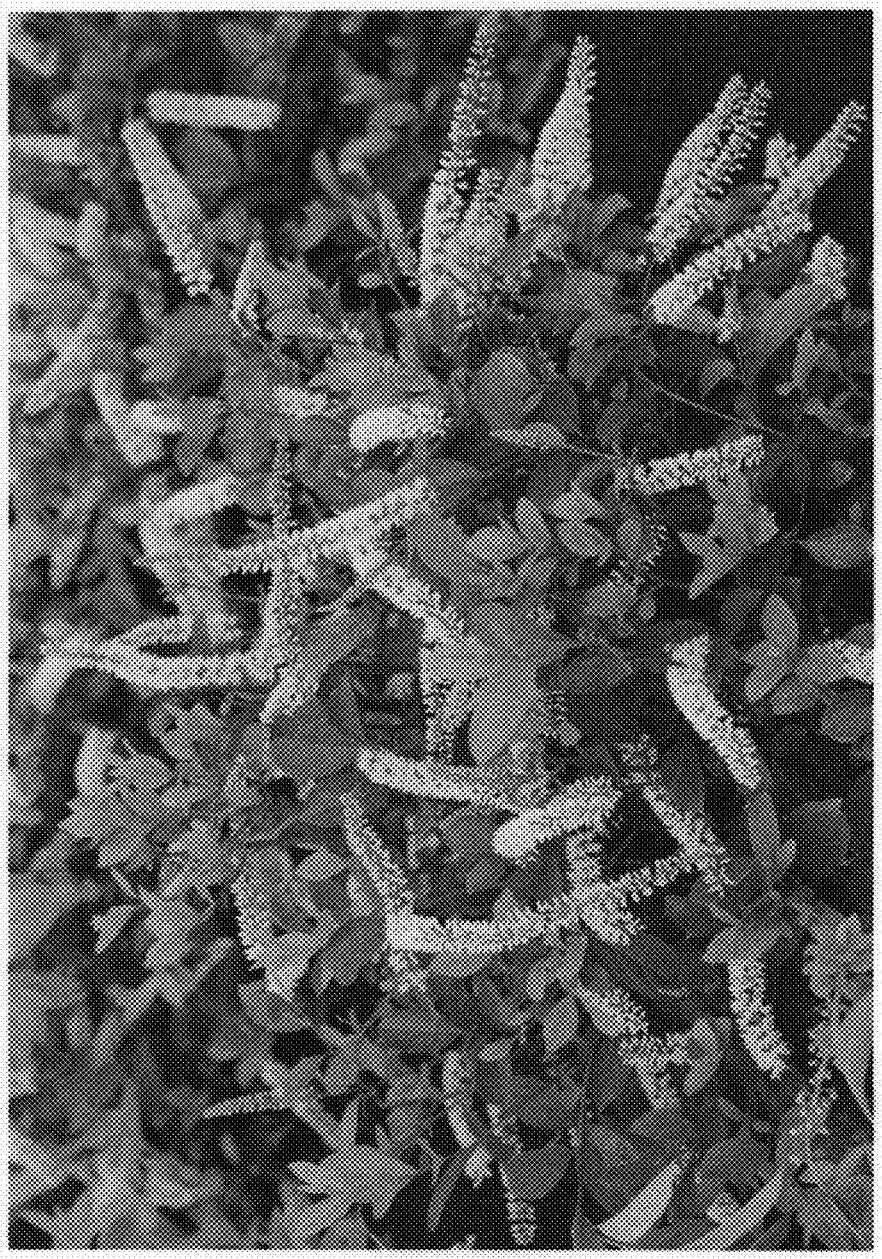

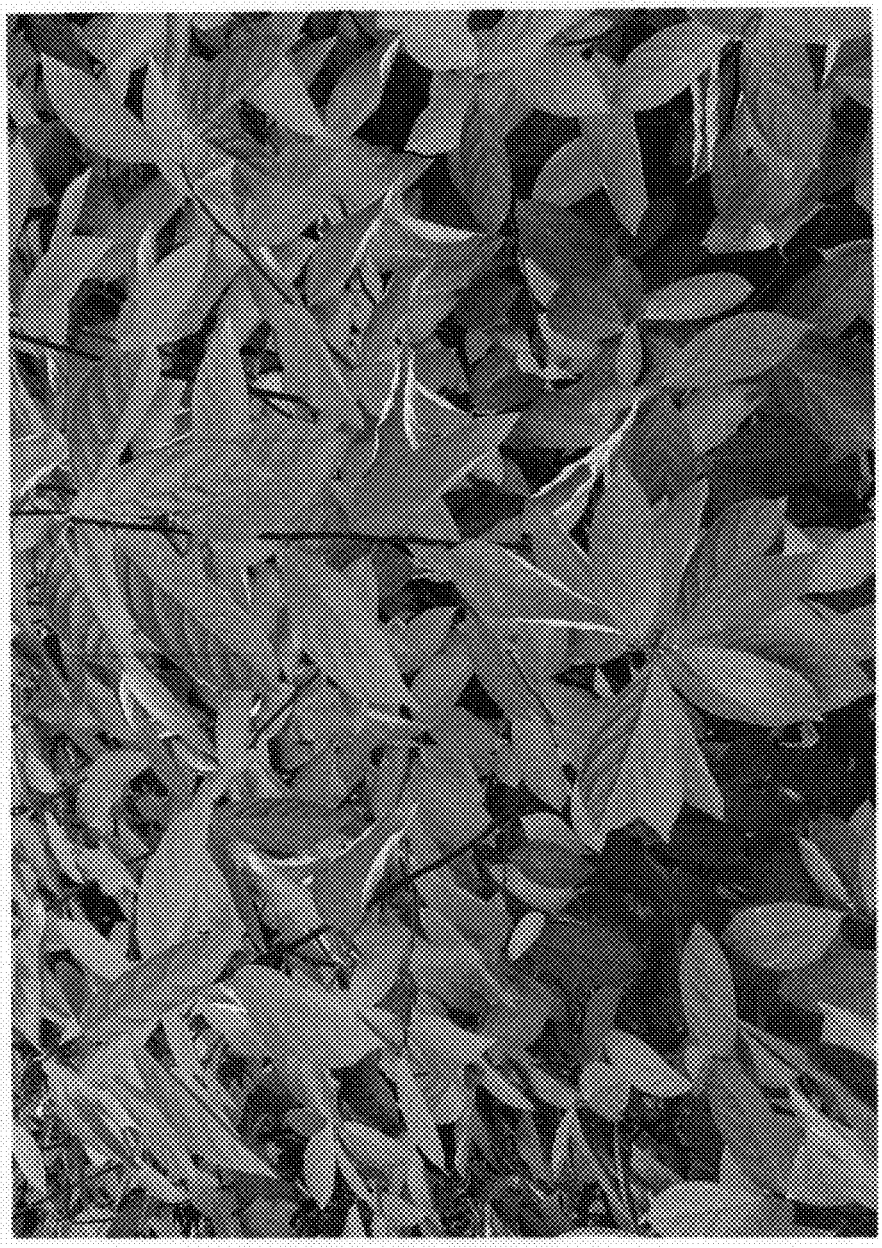

* * * * *